US010562844B2

(12) United States Patent
Lowther et al.

(10) Patent No.: US 10,562,844 B2
(45) Date of Patent: Feb. 18, 2020

(54) HYPDH INHIBITORS AND METHODS OF USE FOR THE TREATMENT OF KIDNEY STONES

(71) Applicants: Wake Forest University Health Sciences, Winston-Salem, NC (US); UAB Research Foundation, Birmingham, AL (US)

(72) Inventors: W. Todd Lowther, Pfafftown, NC (US); Ross P. Holmes, Birmingham, AL (US); Daniel Yohannes, Winston-Salem, NC (US)

(73) Assignees: Wake Forest University Health Sciences, Winston-Salem, NC (US); UAB Research Foundation, Birmingham, AL (US)

( * ) Notice: Subject to any disclaimer, the term of this patent is extended or adjusted under 35 U.S.C. 154(b) by 49 days.

(21) Appl. No.: 15/545,818

(22) PCT Filed: Jan. 25, 2016

(86) PCT No.: PCT/US2016/014707
§ 371 (c)(1),
(2) Date: Jul. 24, 2017

(87) PCT Pub. No.: WO2016/123012
PCT Pub. Date: Aug. 4, 2016

(65) Prior Publication Data
US 2018/0002275 A1  Jan. 4, 2018

Related U.S. Application Data

(60) Provisional application No. 62/107,701, filed on Jan. 26, 2015.

(51) Int. Cl.
| *C07D 333/38* | (2006.01) |
| *C07C 229/48* | (2006.01) |
| *C07D 233/90* | (2006.01) |
| *C07D 307/24* | (2006.01) |
| *C07D 307/68* | (2006.01) |
| *C07C 62/02* | (2006.01) |
| *C07C 62/24* | (2006.01) |
| *C07C 59/11* | (2006.01) |

(52) U.S. Cl.
CPC ............ *C07C 229/48* (2013.01); *C07C 59/11* (2013.01); *C07C 62/02* (2013.01); *C07C 62/24* (2013.01); *C07D 233/90* (2013.01); *C07D 307/24* (2013.01); *C07D 307/68* (2013.01); *C07D 333/38* (2013.01); *C07C 2601/08* (2017.05)

(58) Field of Classification Search
None
See application file for complete search history.

(56) References Cited

U.S. PATENT DOCUMENTS

| 2,475,580 A | 7/1949 | Baker |
| 4,178,386 A | 12/1979 | Williams et al. |
| 4,342,776 A | 8/1982 | Cragoe, Jr. et al. |
| 4,428,959 A | 1/1984 | Cragoe, Jr. et al. |
| 4,432,992 A | 2/1984 | Cragoe, Jr. et al. |
| 4,537,902 A | 8/1985 | Cragoe, Jr. et al. |
| 4,755,517 A | 7/1988 | Bruns et al. |

FOREIGN PATENT DOCUMENTS

WO     WO 03/044015 A2     5/2003

OTHER PUBLICATIONS

European Patent Office Supplementary Search Report and Opinion, EP 16743905.8, dated Jul. 6, 2018, 14 pages.
Das BC et al. Design and synthesis of potential new apoptosis agents: hybrid compounds containing perillyl alcohol and new constrained retinoids. Tetrahedron Letters. 2010; 51: 1462-1466.
Gamedze MP et al. Serendipitous synthesis of 3-hydroxy tetrahydrofurans from tin catalyzed sulfonylation of acyclic 1,2,4-triols. Tetrahedron Letters. 2012; 53: 5929-5932.
Herdeis C and Engel W. Synthesis of unnatural 2R,5S-5-hydroxypipecolic acid via homochiral acyliminium ion-pipecolic acids—part III. Tetrahedron Asymmetry. 1991; 2(10: 945-948.
Hunter GA and McNab H. Chemical and spectroscopic properties of the 3-hydroxythiophene [thiopen-3(2H)-one] system. New Journal of Chemistry. 2010; 34: 2558-2563.
Nebbioso A et al. Molecular characterization of an end-residue of humeomics applied to a soil humic acid. RSC Adv. 2014; 4: 23658-23665.
Rekharsky MV et al. Thermodynamic and nuclear magnetic resonance study of the reactions of [alpha]- and [beta]-cyclodextrin with acids, aliphatic amines, and cyclic alcohols. J. Phys. Chem. B. 1997; 101: 87-100.
Robertson FJ and Wu J. Phosphorothioic acids and related compounds as surrogates for H2S-synthesis of chiral tetrahydrothiophenes. J. Am. Chem. Soc. 2012; 134: 2775-2780.
Yadav JS et al. Dy(OTf)3 as a versatile catalyst for the synthesis of 3-pyrrolyl-indolinones and pyrrolyl-indeno[1,2-b]quinoxalines. Tetrahedron Letters. 2007; 48: 3295-3298.
Enholm EJ and Schreier JA. A direct synthesis of [alpha]-keto five- and six-membered cyclic ethers. J. Heterocyclic Chem. 1995; 32: 109-111.
Ichihara A et al. The synthesis of cis- and trans-demethylmuscarines. 1965; 38(7): 1165-1167.
International Search Report and Written Opinion, PCT/US2016/014707, dated Mar. 30, 2016.
PUBCHEM CID: 20362512. Dec. 5, 2007, pp. 1-12 (online), [retrieved on Dec. 23, 2013.] Retrieved from the Internet https://pubchem.ncbi.nim.nih.gov/compound/20362512.

(Continued)

*Primary Examiner* — Jared Barsky
(74) *Attorney, Agent, or Firm* — Myers Bigel, P.A.

(57) ABSTRACT

Provided herein are compounds of Formula (I), Formula (II), and Formula (III), and compositions comprising the same, as well as methods of use thereof for controlling or inhibiting the formation of calcium oxalate kidney stones, inhibiting the production of glyoxylate and/or oxalate, and/or inhibiting hydroxyproline dehydrogenase (HYPDH).

18 Claims, 2 Drawing Sheets

(56) References Cited

OTHER PUBLICATIONS

Watanabe S et al. Identification and characterization of D-hydroxyproline dehydrogenase and D1-pyrroline-4-hydroxy-2-carboxylate deaminase involved in novel L-hydroxyproline metabolism of bacteria. The Journal of Biological Chemistry. Sep. 21, 2012; 287(39: 32674-32688.

Manfre F et al. Synthesis of proline analogues as potential mechanism-based hinibitors of proline dehydrogenase: 4-methylene-L-, (E)- and (Z)-4-(fluoromethylene)-L-, cis- and trans-5-ethynyl-(±)-, and cis- and trans-5-vinyl-L-proline. J Org Chem. 1992; 57(7): 2060-2065.

Jiang, J., Johnson, L. C., Knight, J., Callahan, M. F., Riedel, T. J., Holmes, R. P., and Lowther, W. T. (2012) Metabolism of [13C5]hydroxyproline in vitro and in vivo: implications for primary hyperoxaluria. Am J Physiol Gastrointest Liver Physiol 302, G637-643.

Knight, J., and Holmes, R. P. (2005) Mitochondrial hydroxyproline metabolism: implications for primary hyperoxaluria. Am J Nephrol 25, 171-175.

Knight, J., Jiang, J., Assimos, D. G., and Holmes, R. P. (2006) Hydroxyproline ingestion and urinary oxalate and glycolate excretion. Kidney Int 70, 1929-1934.

Riedel, T. J., Johnson, L. C., Knight, J., Hantgan, R. R., Holmes, R. P., and Lowther, W. T. (2011) Structural and Biochemical Studies of Human 4-hydroxy-2-oxoglutarate Aldolase: Implications for Hydroxyproline Metabolism in Primary Hyperoxaluria. PLoS One 6, e26021, G637-641.

Knight, J., Holmes, R. P., Cramer, S. D., Takayama, T., and Salido, E. (2012) Hydroxyproline metabolism in mouse models of primary hyperoxaluria. Am J Physiol-Renal 302, F688-693.

Miyata, N., Steffen, J., Johnson, M. E., Fargue, S., Danpure, C. J., and Koehler, C. M. (2014) Pharmacologic rescue of an enzyme-trafficking defect in primary hyperoxaluria 1. Proc Natl Acad Sci USA 111, 14406-14411.

Riedel, T. J., Knight, J., Murray, M. S., Milliner, D. S., Holmes, R. P., and Lowther, W. T. (2012) 4-Hydroxy-2-oxoglutarate aldolase inactivity in primary hyperoxaluria type 3 and glyoxylate reductase inhibition. Biochim Biophys Acta 1822, 1544-1552.

Curhan, G. C., and Taylor, E. N. (2008) 24-h uric acid excretion and the risk of kidney stones. Kidney Int 73, 489-496.

Zhang, Y. (2008) I-TASSER server for protein 3D structure prediction. BMC Bioinformatics 9(40), 8 pages.

Moxley, M. A., and Becker, D. F. (2012) Rapid reaction kinetics of proline dehydrogenase in the multifunctional proline utilization A protein. Biochemistry 51, 511-520.

Moxley, M. A., Tanner, J. J., and Becker, D. F. (2011) Steady-state kinetic mechanism of the proline:ubiquinone oxidoreductase activity of proline utilization A (PutA) from *Escherichia coli*. Arch Biochem Biophys 516, 113-120.

Srivastava, D., Schuermann, J. P., White, T. A., Krishnan, N., Sanyal, N., Hura, G. L., Tan, A., Henzl, M. T., Becker, D. F., and Tanner, J. J. (2010) Crystal structure of the bifunctional proline utilization A flavoenzyme from Bradyrhizobium japonicum. Proceedings of the National Academy of Sciences of the United States of America 107, 2878-2883.

Pemberton, T. A., and Tanner, J. J. (2013) Structural basis of substrate selectivity of Delta(1)-pyrroline-5-carboxylate dehydrogenase (ALDH4A1): semialdehyde chain length. Arch Biochem Biophys 538, 34-40.

Ostrander, E. L., Larson, J. D., Schuermann, J. P., and Tanner, J. J. (2009) A Conserved Active Site Tyrosine Residue of Proline Dehydrogenase Helps Enforce the Preference for Proline over Hydroxyproline as the Substrate. Biochemistry 48, 951-959.

Summitt, C.B. et al. (2015) Proline dehydrogenase 2 (PRODHS)is a hydroxyproline dehydrogenase (HYPDH) and molecular target for treating primary hyperoxaluria. Biochem J. 466, 273-281.

Chetyrkin S.V. et al. (2005) Pyridoxamine lowers kidney crystals in experimental hyperoxaluria: A potential therapy for primary hyperoxaluria. Kidney International 67, 53-60.

Holmes R.P. et al. (2001) (L)-2-oxothiazolidine-4-carboxylate in the treatment of primary hyperoxaluria type 1, RJU International 88, 858-862.

Huffman K.M. et al. (2011) Prodrugs—from serendipity to rational design. Pharmacological Reviews 63(3), 750-771.

Sigma-Aldrich catalog product information, (R)-(-)-2-Oxathiazolidine-4-carboxylic acid. Downloaded from http://www.sigmaaldrich.com on Jan. 9, 2015, 1 page.

Wikipedia, Pyridoxamine. Downloaded from http://en.widipedia.org on Jan. 9, 2015, 5 pages.

HYPDH INHIBITORS AND METHODS OF USE FOR THE TREATMENT OF KIDNEY STONES

RELATED APPLICATIONS

This application is a 35 U.S.C. § 371 national phase entry of PCT Application PCT/US2016/014707, filed Jan. 25, 2016, and published in English on Aug. 4, 2016, as International Publication No. WO 2016/123012, and claims the benefit of U.S. Provisional Patent Application Ser. No. 62/107,701, filed Jan. 26, 2015, the disclosure of each of which is incorporated by reference herein in its entirety.

GOVERNMENT FUNDING

This invention was made with government support under grant numbers DK083527 and DK073732 awarded by National Institutes of Health. The United States government has certain rights in the invention.

BACKGROUND

Kidney stones affect approximately 1 in 11 individuals in the United States. The 2012 National Health and Nutrition and Examination Survey (NHANES), part of the Urological Diseases in America Project, reported that the overall prevalence of kidney stones was 8.8% (10.6% and 7.1% for men and women, respectively) (Jiang et al., Am J Physiol Gastrointest Liver Physiol 302, G637-643, 2012). This study and others attest to the significant increase in stone cases in general, but especially in individuals with obesity, diabetes, and following bariatric surgery (Jiang et al., supra; Knight et al., Am J Nephrol 25, 171-175, 2005). The direct and indirect costs associated with kidney stone treatment (i.e., nephrocalcinosis) are significant (Knight et al., Kidney Int 70, 1929-1934, 2006).

Individuals with Primary Hyperoxaluria (PH) have mutations in a variety of genes involved in glyoxylate and hydroxyproline (Hyp) metabolism that result in a significant increase in oxalate production and deposition of calcium oxalate stones, the most common type of stones for all stone formers. The treatments for these individuals range from a combined kidney-liver transplant to a life-long use of potassium citrate, increased fluid intake and dietary restriction of oxalate (Riedel et al., PLoS One 6, e26021, 2011; Knight et al., Am J Physiol-Renal 302, F688-693, 2012). Treatments for the removal of stones currently include shock-wave lithotripsy, ureteroscopic stone removal, and percutaneous nephrolithotomy (Riedel et al., supra). However, the recurrence of stones following the available procedures is over 50%.

Kidney stones are also a significant problem in veterinary medicine. Pets such as dogs and cats can develop stones that lead to painful urination and/or a life-threatening blockage.

Considering that the current treatments only address symptoms, novel treatments to prevent or control the formation of stones in PH and other idiopathic stone formers are greatly needed.

SUMMARY

Provided herein according to some embodiments is a method of inhibiting the formation of oxalate kidney stones, comprising: administering to a subject in need thereof a therapeutically effective amount of a compound of Formula I, a compound of Formula II, or a compound of Formula III:

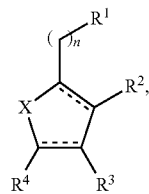

I

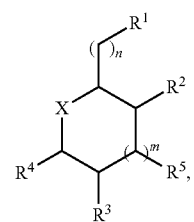

II

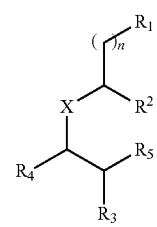

III wherein:

X is O, S, NH, NMe or $CR^xR^y$, wherein $R^x$ and $R^y$ are each independently selected from H, alkyl and halo;

n is 0, 1, 2, 3, 4, 5 or 6;

m is 0, 1, 2, or 3;

$R^1$ is selected from the group consisting of: alkyl, alkenyl, alkynyl, aryl, halo, hydroxy, amine and carboxy;

$R^2$ is selected from the group consisting of: H, alkyl (e.g., lower alkyl), hydroxy, amine, and =O; or $R^2$ is $R^{2a}R^{2b}$, wherein $R^{2a}$ and $R^{2b}$ are each independently selected from alkyl (e.g., lower alkyl) and hydroxy;

$R^3$ is selected from the group consisting of: H, hydroxy, amine, and =O; or $R^3$ is $R^{3a}R^{3b}$, wherein $R^{3a}$ and $R^{3b}$ are each independently selected from alkyl (e.g., lower alkyl) and hydroxy;

$R^4$ is selected from the group consisting of: H, alkyl (e.g., lower alkyl), and hydroxy; or $R^4$ is $R^{4a}R^{4b}$ wherein $R^{4a}$ and $R^{4b}$ are each independently selected from alkyl (e.g., lower alkyl), hydroxy, and halo, wherein said alkyl may be unsubstituted or substituted 1, 2 or 3 times with hydroxy; and each $R^5$ is independently selected from the group consisting of: H, alkyl (e.g., lower alkyl), hydroxy, amine, and =O; or $R^5$ is $R^{5a}R^{5b}$ wherein $R^{5a}$ and $R^{5b}$ are each independently selected from alkyl (e.g., lower alkyl) and hydroxy; or $R^2$ and an adjacent $R^5$ are taken together to form an aryl or heteroaryl, or a pharmaceutically acceptable salt or prodrug thereof.

In some embodiments, the compound is a compound of Formula I:

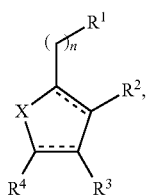

wherein:

X is S;

n is 0;

$R^1$ is selected from the group consisting of: alkyl, alkenyl, alkynyl, aryl, halo, hydroxy, amine and carboxy;

$R^2$ is selected from the group consisting of: H and lower alkyl;

$R^3$ is selected from the group consisting of: hydroxy, amine, and =O; or $R^3$ is $R^{3a}R^{3b}$, wherein $R^{3a}$ and $R^{3b}$ are each independently hydroxy; and $R^4$ is selected from the group consisting of: H and lower alkyl;

or a pharmaceutically acceptable salt or prodrug thereof.

Also provided is a method of inhibiting the production of glyoxylate and/or oxalate in a subject in need thereof, comprising: administering to the subject a therapeutically effective amount of a compound of Formula I, a compound of Formula II, or a compound of Formula III:

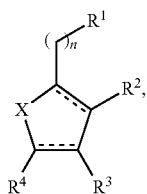

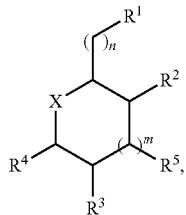

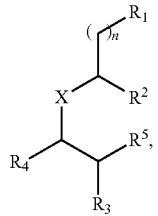

wherein:

X is O, S, NH, NMe or $CR^xR^y$, wherein $R^x$ and $R^y$ are each independently selected from H, alkyl and halo;

n is 0, 1, 2, 3, 4, 5 or 6;

m is 0, 1, 2, or 3;

$R^1$ is selected from the group consisting of: alkyl, alkenyl, alkynyl, aryl, halo, hydroxy, amine and carboxy;

$R^2$ is selected from the group consisting of: H, alkyl (e.g., lower alkyl), hydroxy, amine, and =O; or $R^2$ is $R^{2a}R^{2b}$, wherein $R^{2a}$ and $R^{2b}$ are each independently selected from alkyl (e.g., lower alkyl) and hydroxy;

$R^3$ is selected from the group consisting of: H, hydroxy, amine, and =O; or $R^3$ is $R^{3a}R^{3b}$, wherein $R^{3a}$ and $R^{3b}$ are each independently selected from alkyl (e.g., lower alkyl) and hydroxy;

$R^4$ is selected from the group consisting of: H, alkyl (e.g., lower alkyl), and hydroxy; or $R^4$ is $R^{4a}R^{4b}$ wherein $R^{4a}$ and $R^{4b}$ are each independently selected from alkyl (e.g., lower alkyl), hydroxy, and halo, wherein said alkyl may be unsubstituted or substituted 1, 2 or 3 times with hydroxy; and each $R^5$ is independently selected from the group consisting of: H, alkyl (e.g., lower alkyl), hydroxy, amine, and =O; or $R^5$ is $R^{5a}R^{5b}$ wherein $R^{5a}$ and $R^{5b}$ are each independently selected from alkyl (e.g., lower alkyl) and hydroxy; or $R^2$ and an adjacent $R^5$ are taken together to form an aryl or heteroaryl, or a pharmaceutically acceptable salt or prodrug thereof.

In some embodiments, the compound is a compound of Formula I:

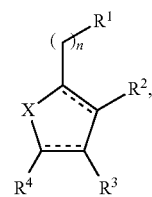

wherein:

X is S;

n is 0;

$R^1$ is selected from the group consisting of: alkyl, alkenyl, alkynyl, aryl, halo, hydroxy, amine and carboxy;

$R^2$ is selected from the group consisting of: H and lower alkyl;

$R^3$ is selected from the group consisting of: hydroxy, amine, and =O; or $R^3$ is $R^{3a}R^{3b}$, wherein $R^{3a}$ and $R^{3b}$ are each independently hydroxy; and $R^4$ is selected from the group consisting of: H and lower alkyl;

or a pharmaceutically acceptable salt or prodrug thereof.

Further provided is a method of inhibiting hydroxyproline dehydrogenase (HYPDH) in a subject in need thereof, comprising: administering to the subject a therapeutically effective amount of a compound of Formula I, a compound of Formula II, or a compound of Formula III:

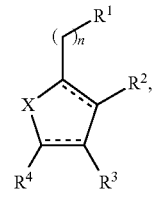

-continued

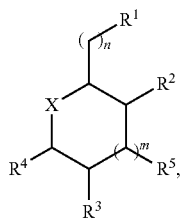

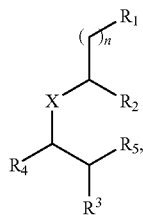

wherein:

X is O, S, NH, NMe or CR$^x$R$^y$, wherein R$^x$ and R$^y$ are each independently selected from H, alkyl and halo;

n is 0, 1, 2, 3, 4, 5 or 6;

m is 0, 1, 2, or 3;

R$^1$ is selected from the group consisting of: alkyl, alkenyl, alkynyl, aryl, halo, hydroxy, amine and carboxy;

R$^2$ is selected from the group consisting of: H, alkyl (e.g., lower alkyl), hydroxy, amine, and =O; or R$^2$ is R$^{2a}$R$^{2b}$, wherein R$^{2a}$ and R$^{2b}$ are each independently selected from alkyl (e.g., lower alkyl) and hydroxy;

R$^3$ is selected from the group consisting of: H, hydroxy, amine, and =O; or R$^3$ is R$^{3a}$R$^{3b}$, wherein R$^{3a}$ and R$^{3b}$ are each independently selected from alkyl (e.g., lower alkyl) and hydroxy;

R$^4$ is selected from the group consisting of: H, alkyl (e.g., lower alkyl), and hydroxy; or R$^4$ is R$^{4a}$R$^{4b}$ wherein R$^{4a}$ and R$^{4b}$ are each independently selected from alkyl (e.g., lower alkyl), hydroxy, and halo, wherein said alkyl may be unsubstituted or substituted 1, 2 or 3 times with hydroxy; and each R$^5$ is independently selected from the group consisting of: H, alkyl (e.g., lower alkyl), hydroxy, amine, and =O; or R$^5$ is R$^{5a}$R$^{5b}$ wherein R$^{5a}$ and R$^{5b}$ are each independently selected from alkyl (e.g., lower alkyl) and hydroxy; or R$^2$ and an adjacent R$^5$ are taken together to form an aryl or heteroaryl, or a pharmaceutically acceptable salt or prodrug thereof.

In some embodiments, the compound is a compound of Formula I:

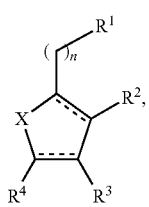

wherein:

X is S;

n is 0;

R$^1$ is selected from the group consisting of: alkyl, alkenyl, alkynyl, aryl, halo, hydroxy, amine and carboxy;

R$^2$ is selected from the group consisting of: H and lower alkyl;

R$^3$ is selected from the group consisting of: hydroxy, amine, and =O; or R$^3$ is R$^{3a}$R$^{3b}$, wherein R$^{3a}$ and R$^{3b}$ are each independently hydroxy; and R$^4$ is selected from the group consisting of: H and lower alkyl;

or a pharmaceutically acceptable salt or prodrug thereof.

Also provided is a compound of Formula I, a compound of Formula II, or a compound of Formula III, or pharmaceutically acceptable salt or prodrug thereof, as well as pharmaceutical compositions comprising the same.

Further provided is the use of a compound of Formula I, a compound of Formula II, or a compound of Formula III, or a pharmaceutically acceptable salt or prodrug thereof, for controlling or inhibiting the formation of calcium oxalate kidney stones, inhibiting the production of glyoxylate and/or oxalate, and/or inhibiting hydroxyproline dehydrogenase (HYPDH).

Also provided is the use of a compound of Formula I, a compound of Formula II, or a compound of Formula III, or a pharmaceutically acceptable salt or prodrug thereof, in the preparation of a medicament for controlling or inhibiting the formation of calcium oxalate kidney stones, inhibiting the production of glyoxylate and/or oxalate, and/or inhibiting hydroxyproline dehydrogenase (HYPDH).

DETAILED DESCRIPTION

Provided herein are methods of treatment for controlling or inhibiting the formation of kidney stones comprising administering to a subject in need thereof an inhibitor of hydroxyproline dehydrogenase (HYPDH), as well as compounds and compositions useful for the same.

The disclosures of all patent references cited herein are hereby incorporated by reference to the extent they are consistent with the disclosure set forth herein. As used herein in the description of the invention and the appended claims, the singular forms "a," "an" and "the" are intended to include the plural forms as well, unless the context clearly indicates otherwise.

"Subject" or "patient" as used herein are generally mammalian subjects, including both human subjects and non-human mammalian subjects (e.g., dog, cat, horse, etc.) for research or veterinary purposes. Subjects may be male or female and may be of any suitable age, including neonate, infant, juvenile, adolescent, adult, and geriatric subjects.

"Treat" as used herein refers to any type of treatment that imparts a benefit to a subject, particularly slowing or inhibiting the formation of glyoxylate and/or oxalate, slowing or inhibiting the formation of calcium oxalate stones in the kidneys and/or urinary tract (kidneys, ureters, bladder, and urethra), and/or the deposition of calcium oxalate in other tissues such as the heart. For example, the treatment may reduce the size of and/or decrease the number of such stones, inhibit or slow the growth of such stones or calcium oxalate deposition in tissues such as the heart, alleviate symptoms of such stones or deposition, etc. Treatment also includes prophylactic treatment of a subject deemed to be at risk of kidney stone formation (e.g., after bariatric surgery).

"Kidney stones" are hard deposits of minerals that form a stone or crystal aggregation, which may result in damage or failure of the kidney and/or urinary tract function. Most kidney stones are calcium stones, usually in the form of calcium oxalate.

"Oxalate" or "oxalic acid" is a dianion of the formula $C_2O_4^{2-}$ produced by the body and also commonly ingested in the diet. Oxalate can combine with calcium in the kidneys or urinary tract to form calcium oxalate, which is the main component of most kidney stones.

Figure 1:
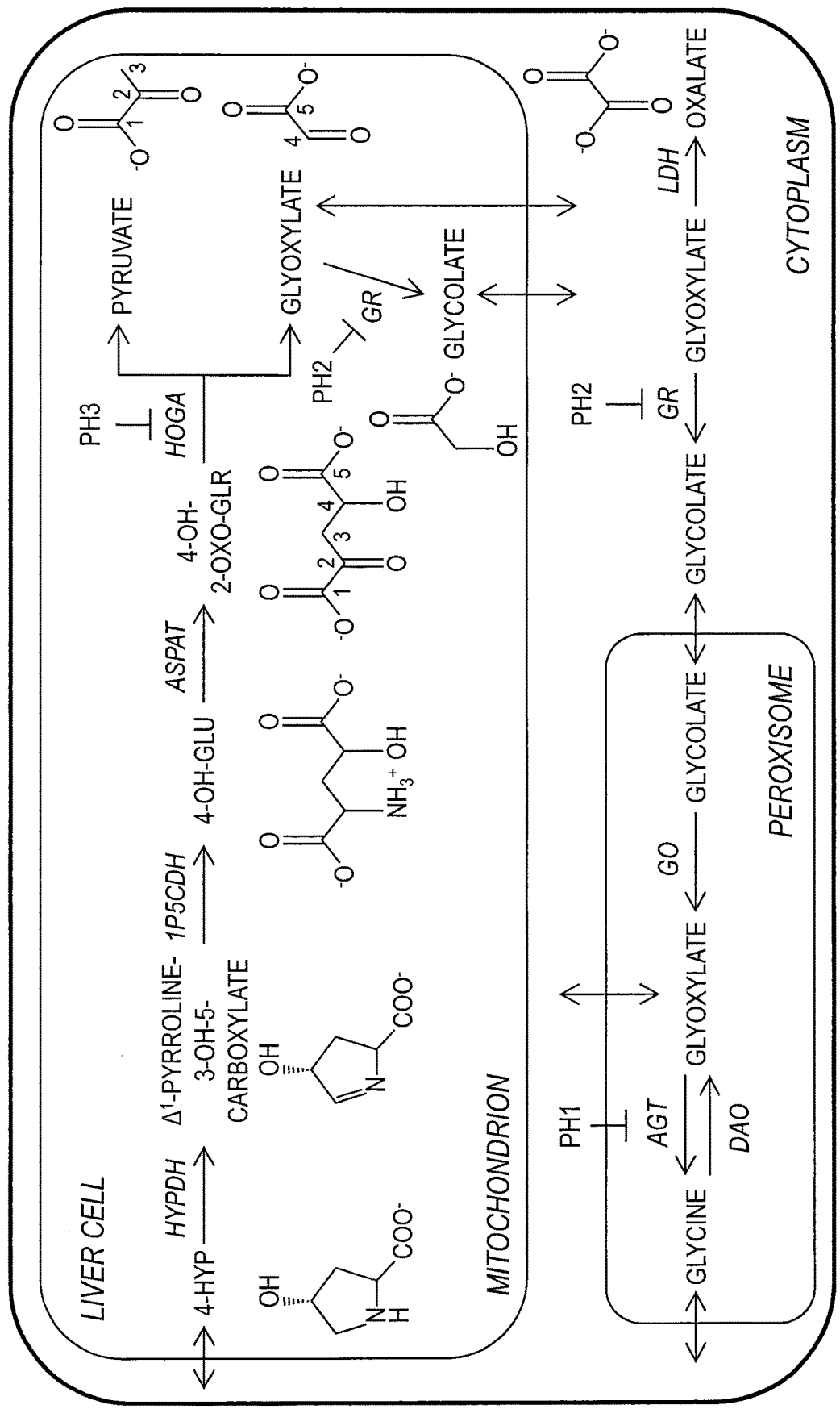
FIG. 1 presents a schematic of the metabolism of 4-hydroxyproline and glyoxylate within a hepatocyte. Four mitochondrial enzymes are responsible for Hyp breakdown: hydroxyproline dehydrogenase (HYPDH), Δ$^1$-pyrroline-5-carboxylate dehydrogenase (1P5CDH), aspartate aminotransferase (AspAT), and 4-hydroxy-2-oxoglutarate aldolase (HOGA). A variety of enzymes, including alanine-glyoxylate aminotransferase (AGT), D-amino acid oxidase (DAO), glyoxylate reductase (GR), and lactate dehydrogenase (LDH), can act on glyoxylate produced from HOG cleavage. AGT, GR, and HOGA are mutated within primary hyperoxaluria patients (type 1, 2, and 3, respectively).

"Glyoxylate" is a precursor of oxalate, as shown in FIG. 1.

"Primary hyperoxaluria" is a condition characterized by the overproduction of oxalate and/or defective production or function of one or more enzymes that regulate the levels of oxalate in the body. Sufferers of Type 1 primary hyperoxaluria have a defect or shortage of the alanine:glyoxylate aminotransferase enzyme (AGT). Type 2 primary hyperoxaluria sufferers have a defect or shortage of the glyoxylate reductase enzyme (GR). Type 3 primary hyperoxaluria sufferers have a defect or shortage of the 4-hydroxy-2-oxoglutarate aldolase (HOGA).

"Hydroxyproline" or "Hyp" has the structure:

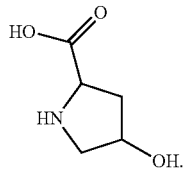

Hydroxyproline is produced in the body primarily from endogenous collagen turnover (Miyata et al., Proc Natl Acad Sci USA 111, 14406-14411, 2014). Using a unique metabolic tracer, $^{13}C_5$, $^{15}N$-Hyp (all five carbons isotope and nitrogen atom labeled), it was determined that the level of Hyp turnover could be as high as 6-7 g/day (Riedel et al., Biochim Biophys Acta 1822, 1544-1552, 2012). Less than 5 mg of free Hyp is excreted in urine each day, indicating that most of the Hyp is metabolized (Belostotsky et al., J Mol Med (Berl) 90, 1497-1504, 2012). This significant metabolic load could contribute up to 25% of the endogenous oxalate produced (Phang et al., (2001) Disorders of proline and hydroxyproline metabolism. in The Metabolic and Molecular Bases of Inherited Disease (Scriver, C. R., Beaudet, A. L., Sly, W. S., Vallee, D., Childs, B., Kinzler, K. W., and Vogelstein, B. eds.), McGraw-Hill, New York. pp 1821-1838). The biological reason why Hyp metabolism occurs is not clear, although it does enable some pyruvate to feed back into other pathways.

Hyp is metabolized primarily in the mitochondria of the liver and renal cortical tissue (Kivirikko, Int Rev Connect Tissue Res 5, 93-163, 1970; Atlante et al., Biochem Biophys Res Commun 202, 58-64, 1994; Monico et al., Clin J Am Soc Nepthrol 6, 2289-2295, 2011; Wold et al., J Food Sc 64, 377-383, 1999). Diet can also be a source of collagen. For example, a quarter pound hamburger rich in gristle could contain as much as 6 grams of collagen, yielding 780 mg of Hyp (Khan et al., J Urol 184, 1189-1196, 2010). In fact, dietary Hyp can significantly increase oxalate production in humans and lead to hyperoxaluria in mouse and rat models (Khan et al., Kidney Int 70, 914-923, 2006; Valle et al., J Clin Invest 64, 1365-1370, 1979; Adams et al., Annu Rev Biochem 49, 1005-1061, 1980).

FIG. 1 presents the Hyp catabolic pathway, which involves four enzymatic reactions (Miyata et al., Proc Natl Acad Sci USA 111, 14406-14411, 2014; Efron et al., New Engl J Med 272, 1299-1309, 1965; Pelkonen et al., New Engl J Med 283, 451-456, 1970). The first step of the pathway is the flavin FAD+-dependent oxidation of Hyp to $\Delta^1$-pyrroline-3-hydroxy-5-carboxylate (3-OH—P5C) by HYPDH. The 3-OH—P5C intermediate is converted to 4-hydroxy-glutamate (4-OH-Glu) by 1P5C dehydrogenase (1P5CDH), an NAD+-dependent enzyme shared with the proline degradation pathway (Efron et al., supra). Aspartate aminotransferase (AspAT) utilizes oxaloacetate to convert 4-OH-Glu to 4-hydroxy-2-oxoglutarate (HOG). HOG is then cleaved by the unique HOG aldolase (HOGA) into two fragments, glyoxylate and pyruvate. The glyoxylate can then be converted to glycolate and glycine via glyoxylate-reductase (GR) and alanine:glyoxylate aminotransferase (AGT), respectively.

AGT, GR, and HOGA are mutated within primary hyperoxaluria patients (PH type 1, 2, and 3, respectively). For PH1 and PH2 patients, the glyoxylate produced from Hyp could exacerbate the already high levels of glyoxylate, and increase oxalate production via the lactate dehydrogenase (LDH). For PH3 patients, HOGA is inactivated, leading to a buildup of HOG (Riedel et al., Biochim Biophys Acta 1822, 1544-1552, 2012; Belostotsky et al., J Mol Med (Berl) 90, 1497-1504, 2012). Recent studies identified that HOG can inhibit GR, potentially leading to a PH2-like phenotype (Riedel et al., Biochim Biophys Acta 1822, 1544-1552, 2012).

In contrast, hydroxyprolinemia, caused by deficiencies in HYPDH, is not associated with any overt consequences, and Hyp is safely excreted without being degraded (Curhan et al., Kidney Int 73, 489-496, 2008; Roy et al., Nature Protoc 5, 725-738, 2010).

Thus, and without wishing to be bound by theory, inhibition of HYPDH by a small molecule inhibitor is not expected to lead to any adverse side effects, and will block the formation of glyoxylate and oxalate from Hyp for all PH patient types and the buildup of HOG, 4-OH-Glu and dihydroxy-glutarate for PH3 patients.

Inhibition of HYPDH is also expected to help idiopathic stone formers and other individuals with high urinary oxalate levels, such as those that have undergone gastric bypass surgery. For the latter, there is a significant increase in stone formation that may benefit from prophylactic treatment post surgery. While the exact origins of the oxalate in these patients has not been determined, inhibition of HYPDH will decrease glyoxylate and oxalate levels, which will ultimately reduce the glyoxylate and oxalate burden in them.

1. Active Compounds.

As used herein in the accompanying chemical structures, "H" refers to a hydrogen atom. "C" refers to a carbon atom. "N" refers to a nitrogen atom. "O" refers to an oxygen atom. "Me" refers to a methyl group.

The term "hydroxy," as used herein, refers to a group —OH.

"Carbonyl" is a group having a carbon atom double-bonded to an oxygen atom (C=O).

"Carboxy" as used herein refers to a group —COOH.

"Amine" or "amino" refers to a group —NH$_2$.

"Halo" is a halogen group selected from the group consisting of fluoro (—F), choro (—Cl), bromo (—Br), and iodo (—I).

"Alkyl," as used herein, refers to a saturated straight or branched chain, or cyclic hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, cyclopropyl, cyclobutyl, cyclopentyl, cyclohexyl, and the like. "Lower alkyl" as used herein, is a subset of alkyl and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, cyclopropyl, cyclobutyl, and the like.

"Alkenyl," as used herein, refers to a straight or branched chain hydrocarbon containing from 2 to 10 carbons and containing at least one carbon-carbon double bond formed by the removal of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like. "Lower alkenyl" as used herein, is a subset of alkenyl and refers to a straight or branched chain hydrocarbon group containing from 2 to 4 carbon atoms and at least one carbon-carbon double bond.

"Alkynyl," as used herein, refers to a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, 1-butynyl and the like. "Lower alkynyl" as used herein, is a subset of alkynyl and refers to a straight or branched chain hydrocarbon group containing from 2 to 4 carbon atoms at least one carbon-carbon triple bond.

"Aryl," as used herein, refers to a monocyclic carbocyclic ring system or a bicyclic carbocyclic fused ring system having one or more aromatic rings. Representative examples of aryl include the monovalent species azulenyl, indanyl, indenyl, naphthyl, phenyl, tetrahydronaphthyl, and the like, or divalent species thereof if formed from R$^2$ and an adjacent R$^5$ taken together in Formula II as taught herein.

"Heteroaryl," as used herein, refers to a monovalent aromatic group having a single ring or two fused rings and containing in the ring(s) at least one heteroatom (typically 1 to 3) selected from nitrogen, oxygen or sulfur. Representative heteroaryl groups include, by way of example, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzoimidazole, benzthiazole, quinoline, isoquinoline, quinazoline, quinoxaline and the like, or divalent species thereof if formed from R$^2$ and an adjacent R$^5$ taken together in Formula II as taught herein.

As used herein, a specified group may be either unsubstituted, or substituted by one or more suitable groups in place of a hydrogen atom on the parent chain or cycle of an organic molecule. For example, the alkyl, alkenyl, alkynyl, aryl and heteroaryl groups of the invention may be unsubstituted or substituted (e.g., 1, 2 or 3 times) with alkyl, hydroxy or halo.

A "pharmaceutically acceptable salt" is a salt that retains the biological effectiveness of the free acids or bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methane-sulfonates, propanesulfonates, naphthalene-1-sulfonates, naphthalene-2-sulfonates, and mandelates.

A "prodrug" is a compound that is converted under physiological conditions or by solvolysis or metabolically to a compound that is pharmaceutically active. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein in their entirety. See also Huttunen et al., "Prodrugs—from Serendipity to Rational Design," Pharmacological Reviews 63(3):750-771 (2011), which is incorporated by reference herein. Example prodrugs include, but are not limited to, the addition of/conversion to phosphate(s), amino acid esters, amino acid amides, sugar derivatives, alkyl or aryl esters, etc., at an —OH, —SH, —NH or —COOH group of the parent active compound.

Provided herein as active compounds according to some embodiments are compounds of Formula I:

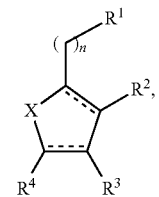

wherein:

X is O, S, NH, NMe or CR$^x$R$^y$, wherein R$^x$ and R$^y$ are each independently selected from H, alkyl and halo;

n is 0, 1, 2, 3, 4, 5 or 6;

R$^1$ is selected from the group consisting of: alkyl, alkenyl, alkynyl, aryl, halo, hydroxy, amine and carboxy;

R$^2$ is selected from the group consisting of: H, alkyl (e.g., lower alkyl), hydroxy, amine, and =O; or R$^2$ is R$^{2a}$R$^{2b}$, wherein R$^{2a}$ and R$^{2b}$ are each independently selected from alkyl (e.g., lower alkyl) and hydroxy;

R$^3$ is selected from the group consisting of: hydroxy, amine, and =O; or R$^3$ is R$^{3a}$R$^{3b}$, wherein R$^{3a}$ and R$^{3b}$ are each independently hydroxy; and R$^4$ is selected from the group consisting of: H, alkyl (e.g., lower alkyl), and hydroxy; or R$^4$ is R$^{4a}$R$^{4b}$ wherein R$^{4a}$ and R$^{4b}$ are each independently selected from alkyl (e.g., lower alkyl), hydroxy, and halo, wherein said alkyl may be unsubstituted or substituted 1, 2 or 3 times with hydroxy, or a pharmaceutically acceptable salt or prodrug thereof.

In some embodiments of Formula I, X is O, S, or CR$^x$R$^y$.

In some embodiments of Formula I, n is 0 and/or R$^1$ is hydroxy.

In some embodiments of Formula I, $R^2$ and/or $R^4$ is selected from the group consisting of: H and lower alkyl.

In some embodiments of Formula I, $R^3$ is hydroxy.

In some embodiments, of Formula I, the compound is a compound of Formula I(A):

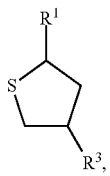

I(A)

wherein:

$R^1$ is selected from the group consisting of: alkyl, alkenyl, alkynyl, aryl, halo, hydroxy, amine and carboxy; and $R^3$ is selected from the group consisting of: H, hydroxy, amine, and =O; or $R^3$ is $R^{3a}R^{3b}$, wherein $R^{3a}$ and $R^{3b}$ are each independently selected from alkyl (e.g., lower alkyl) and hydroxy;

or a pharmaceutically acceptable salt or prodrug thereof.

In some embodiments of Formula I(A), $R^1$ is carboxy and/or $R^3$ is hydroxy or $R^{3a}R^{3b}$, wherein $R^{3a}$ and $R^{3b}$ are each hydroxy.

Also provided herein are compounds of Formula II:

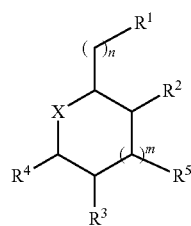

II wherein:

X is O, S, NH, NMe or $CR^xR^y$, wherein $R^x$ and $R^y$ are each independently selected from H, alkyl and halo;

n is 0, 1, 2, 3, 4, 5 or 6;

m is 0, 1, 2, or 3;

$R^1$ is selected from the group consisting of: alkyl, alkenyl, alkynyl, aryl, halo, hydroxy, amine and carboxy;

$R^2$ is selected from the group consisting of: H, alkyl (e.g., lower alkyl), hydroxy, amine, and =O; or $R^2$ is $R^{2a}R^{2b}$, wherein $R^{2a}$ and $R^{2b}$ are each independently selected from alkyl (e.g., lower alkyl) and hydroxy;

$R^3$ is selected from the group consisting of: H, hydroxy, amine, and =O; or $R^3$ is $R^{3a}R^{3b}$, wherein $R^{3a}$ and $R^{3b}$ are each independently selected from alkyl (e.g., lower alkyl) and hydroxy;

$R^4$ is selected from the group consisting of: H, alkyl (e.g., lower alkyl), and hydroxy; or $R^4$ is $R^{4a}R^{4b}$ wherein $R^{4a}$ and $R^{4b}$ are each independently selected from alkyl (e.g., lower alkyl), hydroxy, and halo, wherein said alkyl may be unsubstituted or substituted 1, 2 or 3 times with hydroxy; and each $R^5$ is independently selected from the group consisting of: H, alkyl (e.g., lower alkyl), hydroxy, amine, and =O; or $R^5$ is $R^{5a}R^{5b}$ wherein $R^{5a}$ and $R^{5b}$ are each independently selected from alkyl (e.g., lower alkyl) and hydroxy; or $R^2$ and an adjacent $R^5$ are taken together to form an aryl or heteroaryl, or a pharmaceutically acceptable salt or prodrug thereof.

In some embodiments of Formula II, X is O, NH, NMe or $CR^xR^y$.

In some embodiments of Formula II, n is 0 and/or $R^1$ is hydroxy.

In some embodiments of Formula II, $R^2$ and/or $R^4$ is selected from the group consisting of: H and lower alkyl.

In some embodiments of Formula II, $R^3$ is hydroxy.

In some embodiments of Formula II, $R^2$ is selected from the group consisting of: H, hydroxy, and lower alkyl.

Further provided herein are compounds of Formula III:

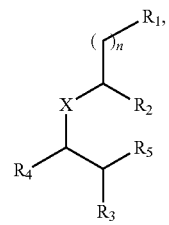

III wherein:

X is O, S, NH, NMe or $CR^xR^y$, wherein $R^x$ and $R^y$ are each independently selected from H, alkyl and halo;

n is 0, 1, 2, 3, 4, 5 or 6;

$R^1$ is selected from the group consisting of: alkyl, alkenyl, alkynyl, aryl, halo, hydroxy, amine and carboxy;

$R^2$ is selected from the group consisting of: H, alkyl (e.g., lower alkyl), hydroxy, amine, and =O; or $R^2$ is $R^{2a}R^{2b}$, wherein $R^{2a}$ and $R^{2b}$ are each independently selected from alkyl (e.g., lower alkyl) and hydroxy;

$R^3$ is selected from the group consisting of: H, hydroxy, amine, and =O; or $R^3$ is $R^{3a}R^{3b}$, wherein $R^{3a}$ and $R^{3b}$ are each independently selected from alkyl (e.g., lower alkyl) and hydroxy;

$R^4$ is selected from the group consisting of: H, alkyl (e.g., lower alkyl), and hydroxy; or $R^4$ is $R^{4a}R^{4b}$ wherein $R^{4a}$ and $R^{4b}$ are each independently selected from alkyl (e.g., lower alkyl), hydroxy, and halo, wherein said alkyl may be unsubstituted or substituted 1, 2 or 3 times with hydroxy; and $R^5$ is independently selected from the group consisting of: H, alkyl (e.g., lower alkyl), hydroxy, amine, and =O; or $R^5$ is $R^{5a}R^{5b}$ wherein $R^{5a}$ and $R^{5b}$ are each independently selected from alkyl (e.g., lower alkyl) and hydroxy, or a pharmaceutically acceptable salt or prodrug thereof.

In some embodiments of Formula III, X is NH.

In some embodiments of Formula III, n is 0 and/or $R^1$ is hydroxy.

In some embodiments of Formula III, $R^2$ and/or $R^4$ is selected from the group consisting of: H and lower alkyl.

In some embodiments of Formula III, $R^3$ is hydroxy.

2. Formulations.

The active compounds described herein may be formulated for administration in a pharmaceutical carrier in accordance with known techniques. See, e.g., Remington, *The Science And Practice of Pharmacy* (9th Ed. 1995). In the manufacture of a pharmaceutical formulation according to the invention, the active compound (including the physiologically acceptable salts or prodrugs thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active agent. One or more active agents may be incorporated in the formulations of the invention, which may be prepared by any of the well-known techniques of pharmacy comprising admixing the components, optionally including one or more accessory ingredients.

The pharmaceutical compositions may also contain other additives, such as pH-adjusting additives. In particular, useful pH-adjusting agents include acids, such as hydrochloric acid, bases and/or buffers, such as sodium lactate, sodium acetate, sodium phosphate, sodium citrate, sodium borate, or sodium gluconate. Further, the compositions may contain preservatives. Useful preservatives include methylparaben, propylparaben, benzoic acid and benzyl alcohol.

Formulations of the invention include those suitable for oral, buccal (sub-lingual), parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound being used.

Formulations suitable for oral administration may be presented in discrete units, such as capsules, cachets, lozenges, or tablets, each containing a predetermined amount of the active compound(s); as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for oral administration also include food product formulations, such as a nutritional bar or an animal feed (e.g., pet food such as dog or cat food). Food product formulations may include one or more of carbohydrates such as wheat, corn rice, barley or oats, dairy products such as milk, oils such as canola oil or soybean oil, flavorants such as sugar or syrup, coloring, chocolate, preservatives, etc. Pet food formulations, in particular, may include meat, poultry, fish or other animal-derived components such as eggs.

Formulations suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound(s) in a unit dosage form in a sealed container. The active compound(s) may be provided in the form of a lyophilizate which is capable of being reconstituted with a suitable pharmaceutically acceptable carrier to form a liquid composition suitable for injection thereof into a subject.

When the active compound(s) is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

The unit dosage form typically comprises from about 1 mg, 5 mg, 10 mg, 100 mg, 250 mg, 500 mg, 1 gram, 5 grams, 10 grams, or any ranges therein, of the active compound(s), depending on the subject being treated (e.g., human or non-human mammalian subject). In some embodiments, the unit dosage form is in the range of 500 mg to 10 grams, keeping in mind that a good portion of the active compound(s) may not be absorbed upon administration (e.g., oral administration).

The present invention is explained in greater detail in the following non-limiting examples.

EXAMPLES

Example 1. Measurement of Hydroxyproline Metabolism

Patients with PH1, PH2, and PH3 and normal subjects were placed on a 3-day controlled diet and infused in the fasted state with $^{15}$N-$^{13}$C$_5$-Hyp at a constant rate (750 nmol/kg/h) for 6 h. Urine and plasma samples were collected hourly for analysis: total $^{13}$C-labelled Hyp and glycine by GC/MS; oxalate and glycolate by IC and IC/MS. The tracer has proven to work effectively and safely. The tracer did not change the pre-infusion and post-infusion total urinary oxalate excretion (e.g., 13±3 versus 9±4 mg/g creat/h for normal; 60±50 versus 40±29 mg/g creat/h for PH1; similar values for PH2 and PH3 samples).

A preliminary comparison of the enrichment of the tracer in plasma Hyp, urine oxalate, and urine glycolate reveals intriguing patterns and highlights the degree to which Hyp metabolism in PH1-3 patients is different. The preliminary data indicate that the plasma levels of $^{15}$N-$^{13}$C$_5$-Hyp in PH1 and PH3 patients is enriched over controls (~2-fold). This may suggest that Hyp turnover is slower in these patients; however, the range of values for the patients tested is quite wide, and overlaps with the control values (hence, the need to know which PH1 mutations are present and the treatment regimen). There is also the possibility that collagen breakdown by collagenases may be yielding a spectrum of peptides that may be metabolized more quickly and partition differently in plasma than free Hyp.

Notably, the proportion of the label in urine oxalate is significantly increased in all PH patient groups (2- to 8-fold), with PH3 being the highest. This observation supports that HOG is being broken down in PH3 patients by another pathway to glyoxylate/oxalate.

Altogether, these observations suggest that Hyp contributes up to 25% of urinary oxalate.

An increase in the level of urine oxalate, on the order of 3-5 mg/day, can have up to a 2-fold increase in stone disease risk (Zhang, BMC Bioinformatics 9, 40, 2008). Therefore, blocking HYPDH activity has the potential to decrease the amount of glyoxylate and oxalate produced endogenously by all three types of PH patients, and to markedly reduce their risk for stone formation and disease. Similarly, HYPDH inhibition may also benefit idiopathic stone formers and other individuals with high urinary oxalate levels, such as those that have undergone gastric bypass surgery. For the latter, there is a significant increase in stone formation that may benefit from prophylactic treatment post surgery. While the exact origins of the oxalate in these patients has not been determined, inhibition of HYPDH will decrease glyoxylate and oxalate levels, which will ultimately reduce the glyoxylate and oxalate burden in them.

Example 2. Development of Recombinant, Human HYPDH and Activity Assay

Despite the identification of the Hyp pathway in rat and bovine kidneys and livers over 50 years ago, very little is known about human HYPDH (also known as PRODH2 and hydroxyproline oxidase, HPOX, in the literature) (Miyata et al., Proc Natl Acad Sci USA 111, 14406-14411, 2014; Efron et al., New Engl J Med 272, 1299-1309; Pelkonen et al., New Engl J Med 283, 451-456, 1970). In an effort to biochemically and structurally characterize human HYPDH, we have evaluated numerous expression constructs (>15) in *Escherichia coli* with N- and C-terminal truncations. These constructs exhibit different levels of protein production, solubility (i.e., inclusion body formation), FAD+ cofactor loading, and enzymatic activity. Only the constructs containing the residues 147-515 and 156-515 were >96% loaded with FAD+ and active.

Recombinant HYPDH: (1) displays typical FAD spectra upon oxidation and reduction, (2) exhibits kinetic parameters for the turnover of Hyp consistent with homologs (Zhang, BMC Bioinformatics 9, 40, 2008; Moxley et al., Biochemistry 51, 511-520, 2012; Moxley et al., Arch Biochem Biophys 516, 113-120, 2011; Srivastava et al., Proc Natl Acad Sci USA 107, 2878-2883, 2010), (3) is selective for Hyp and not Pro, (4) readily uses a variety of CoQ10 analogs as an electron acceptor during catalysis, and (5) binds Hyp with a KD value of 125 µM, using an anaerobic titration of the FAD+ spectrum. These data represent the first biochemical data available for human HYPDH by any laboratory.

Example 3. Identification and Testing of Inhibitors of HYPDH

Figure 2:
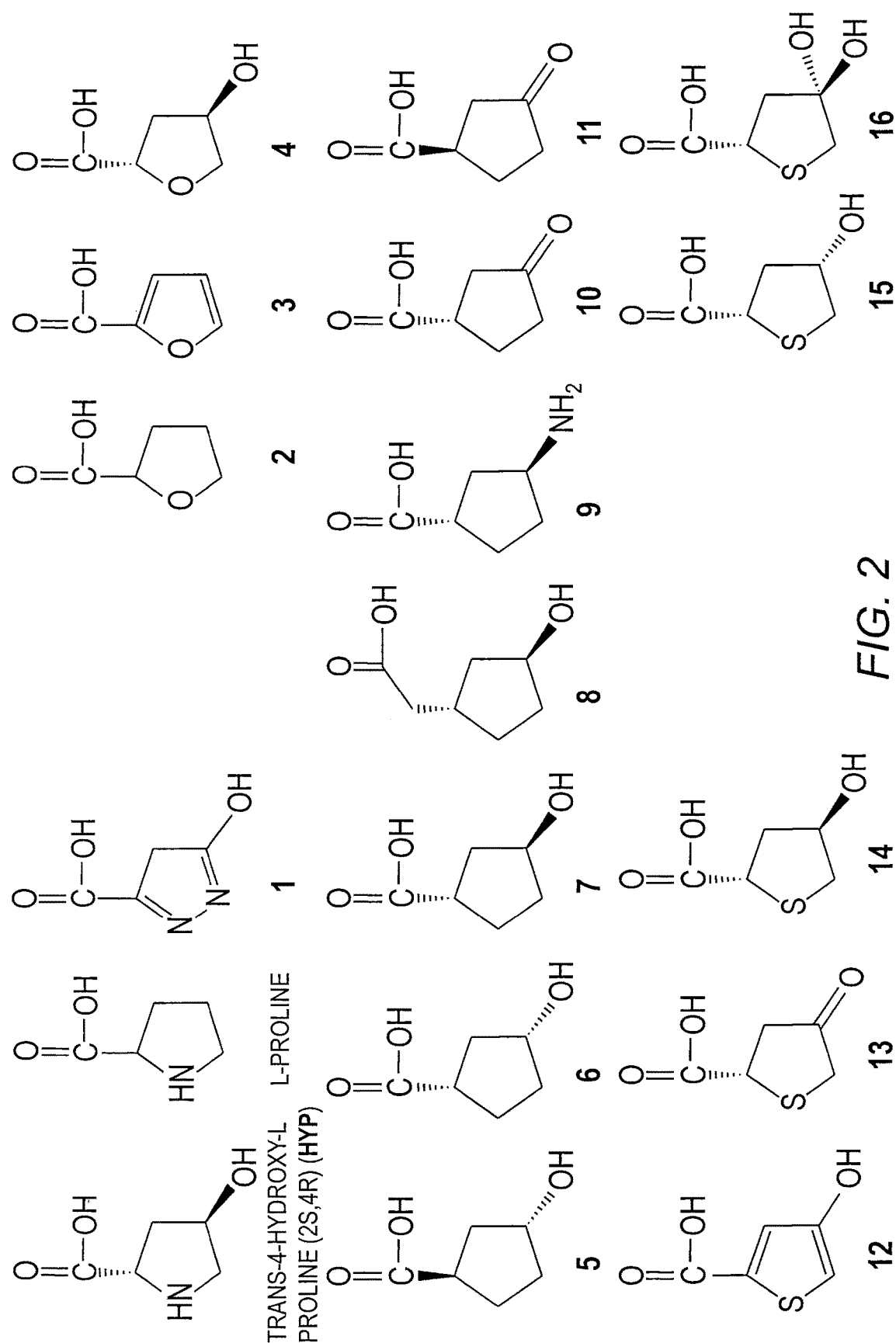
FIG. 2 presents the structures of Hyp analogs, of which some have been tested for HYPDH inhibition.

Tested compounds are shown in FIG. 2. Some compounds were commercially available, and non-commercial compounds were synthesized on a fee-for-service basis contract with Jasco Pharmaceuticals (Woburn, Mass.). Compound 3 is not yet tested, and compound 4 is not yet synthesized.

Each inhibitor was pre-incubated with HYPDH for 5 min, and the reaction started by the addition of 600 mM Hyp. A range of concentrations was tested in order to determine the IC50 value. Table 1 lists the potency of the compounds.

TABLE 1

| Cmpd | IC$_{50}$ (mM) |
|---|---|
| 1 | 2.9 ± 0.1 |
| 5 | 2.1 ± 0.1 |
| 2 | 1.5 ± 0.1 |
| 3 | ND$^a$ |
| 4 | ND$^b$ |
| 9 | 0.63 ± 0.01 |
| 6 | >10 |
| 7 | 0.60 ± 0.01 |
| 10 | 0.38 ± 0.01 |
| 11 | 0.37 ± 0.01 |
| 8 | 0.48 ± 0.01 |
| 13 | 0.32 ± 0.01 |
| 12 | <1 |
| 15 | 0.37 ± 0.01 |
| 14 | 0.33 ± 0.01 |
| 16 | 0.29 ± 0.01 |

$^a$Not soluble in buffer
$^b$Synthesis planned

Inhibitors of HYPDH were identified as compounds in which the nitrogen atom of the Hyp ring is changed to oxygen, carbon or sulfur. This substitution prevents ring oxidation and cleavage by HYPDH. The data indicate that the most potent compounds belong to the reduced thiophene class, closely followed by the cyclopentane analogs.

Example 4. Further Testing of Inhibitors of HYPDH

Additional compounds are obtained, and tested in the same manner as in Example 3 above. These additional compounds may include those in Scheme 1:

Scheme 1.

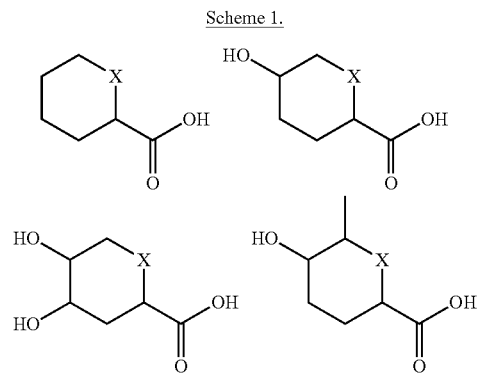

-continued

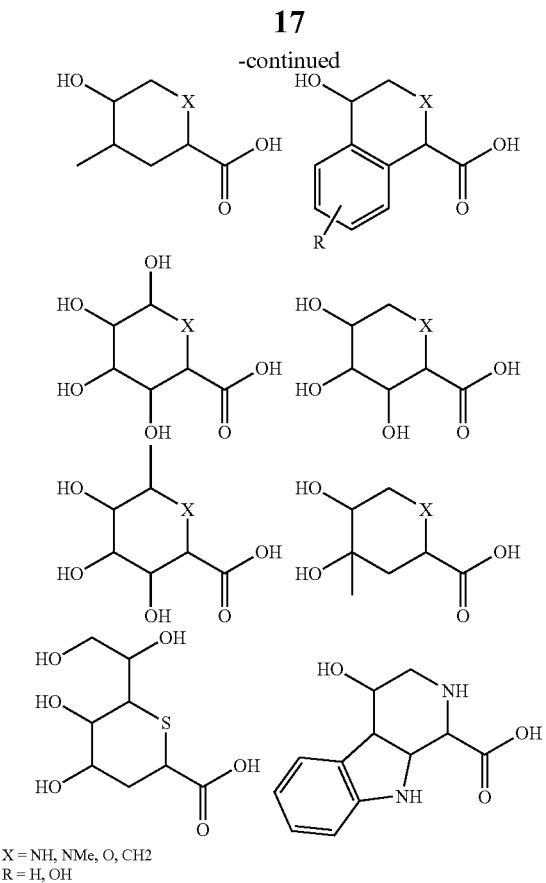

X = NH, NMe, O, CH2
R = H, OH

Additional compounds may also include those in Scheme 2:

Scheme 2.

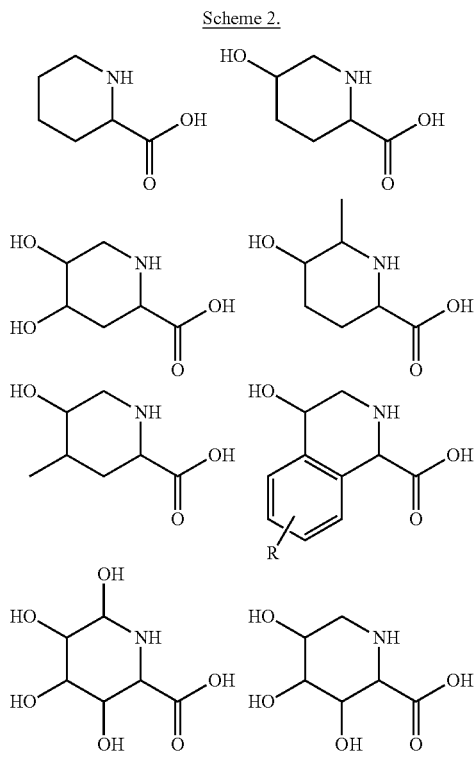

-continued

R = H, OH

LITERATURE CITED

1. Jiang, J., Johnson, L. C., Knight, J., Callahan, M. F., Riedel, T. J., Holmes, R. P., and Lowther, W, T. (2012) Metabolism of [13C5]hydroxyproline in vitro and in vivo: implications for primary hyperoxaluria. Am J Physiol Gastrointest Liver Physiol 302, G637-643
2. Knight, J., and Holmes, R. P. (2005) Mitochondrial hydroxyproline metabolism: implications for primary hyperoxaluria. Am J Nephrol 25, 171-175
3. Knight, J., Jiang, J., Assimos, D. G., and Holmes, R. P. (2006) Hydroxyproline ingestion and urinary oxalate and glycolate excretion. Kidney Int 70, 1929-1934
4. Riedel, T. J., Johnson, L. C., Knight, J., Hantgan, R. R., Holmes, R. P., and Lowther, W. T. (2011) Structural and Biochemical Studies of Human 4-hydroxy-2-oxoglutarate Aldolase: Implications for Hydroxyproline Metabolism in Primary Hyperoxaluria. PLoS One 6, e26021
5. Knight, J., Holmes, R. P., Cramer, S. D., Takayama, T., and Salido, E. (2012) Hydroxyproline metabolism in mouse models of primary hyperoxaluria. Am J Physiol-Renal 302, F688-693
6. Miyata, N., Steffen, J., Johnson, M, E., Fargue, S., Danpure, C. J., and Koehler, C. M. (2014) Pharmacologic rescue of an enzyme-trafficking defect in primary hyperoxaluria 1. Proc Natl Acad Sci USA 111, 14406-14411
7. Riedel, T. J., Knight, J., Murray, M. S., Milliner, D. S., Holmes, R. P., and Lowther, W. T. (2012) 4-Hydroxy-2-oxoglutarate aldolase inactivity in primary hyperoxaluria type 3 and glyoxylate reductase inhibition. Biochim Biophys Acta 1822, 1544-1552
8. Belostotsky, R., Pitt, J. J., and Frishberg, Y. (2012) Primary hyperoxaluria type III—a model for studying perturbations in glyoxylate metabolism. J Mol Med (Berl) 90, 1497-1504
9. Phang, J. M., Hu, C. A., and Valle, D. (2001) Disorders of proline and hydroxyproline metabolism, in The Metabolic and Molecular Bases of Inherited Disease (Scriver, C. R., Beaudet, A. L., Sly, W. S., Vallee, D., Childs, B., Kinzler, K. W., and Vogelstein, B. eds.), McGraw-Hill, New York. pp 1821-1838
10. Kivirikko, K. I. (1970) Urinary excretion of hydroxyproline in health and disease. Int Rev Connect Tissue Res 5, 93-163
11. Atlante, A., Passarella, S., and Quagliariello, E. (1994) Spectroscopic study of hydroxyproline transport in rat kidney mitochondria. Biochem Biophys Res Commun 202, 58-64

12. Monico, C. G., Rossetti, S., Belostotsky, R., Cogal, A. G., Herges, R. M., Seide, B. M., Olson, J. B., Bergstrahl, E. J., Williams, H. J., Haley, W. E., Frishberg, Y., and Milliner, D. S. (2011) Primary hyperoxaluria type III gene HOGA1 (formerly DHDPSL) as a possible risk factor for idiopathic calcium oxalate urolithiasis. Clin J Am Soc Nepthrol 6, 2289-2295

13. Wold, J. P., Lundby, F., and Egelandsdel, B. (1999) Quantification of connective tissue (hydroxyproline) in ground beef by autofluorescence spectroscopy. J Food Sc 64, 377-383

14. Khan, S. R., and Glenton, P. A. (2010) Experimental induction of calcium oxalate nephrolithiasis in mice. J Urol 184, 1189-1196

15. Khan, S. R., Glenton, P. A., and Byer, K. J. (2006) Modeling of hyperoxaluric calcium oxalate nephrolithiasis: experimental induction of hyperoxaluria by hydroxy-L-proline. Kidney Int 70, 914-923

16. Valle, D., Goodman, S. I., Harris, S. C., and Phang, J. M. (1979) Genetic evidence for a common enzyme catalyzing the second step in the degradation of proline and hydroxyproline. J Clin Invest 64, 1365-1370

17. Adams, E., and Frank, L. (1980) Metabolism of proline and the hydroxyprolines. Annu Rev Biochem 49, 1005-1061

18. Efron, M. L., Bixby, E. M., and Pryles, C. V. (1965) Hydroxyprolinemia. Ii. A Rare Metabolic Disease Due to a Deficiency of the Enzyme "Hydroxyproline Oxidase". New Engl J Med 272, 1299-1309

19. Pelkonen, R., and Kivirikko, K. I. (1970) Hydroxyprolinemia: an apparently harmless familial metabolic disorder. New Engl J Med 283, 451-456

20. Curhan, G. C., and Taylor, E. N. (2008) 24-h uric acid excretion and the risk of kidney stones. Kidney Int 73, 489-496

21. Roy, A., Kucukural, A., and Zhang, Y. (2010) I-TASSER: a unified platform for automated protein structure and function prediction. Nature Protoc 5, 725-738

22. Zhang, Y. (2008) I-TASSER server for protein 3D structure prediction. BMC Bioinformatics 9, 40

23. Moxley, M. A., and Becker, D. F. (2012) Rapid reaction kinetics of proline dehydrogenase in the multifunctional proline utilization A protein. Biochemistry 51, 511-520

24. Moxley, M. A., Tanner, J. J., and Becker, D. F. (2011) Steady-state kinetic mechanism of the proline:ubiquinone oxidoreductase activity of proline utilization A (PutA) from *Escherichia coli*. Arch Biochem Biophys 516, 113-120

25. Srivastava, D., Schuermann, J. P., White, T. A., Krishnan, N., Sanyal, N., Hura, G. L., Tan, A., Henzl, M. T., Becker, D. F., and Tanner, J. J. (2010) Crystal structure of the bifunctional proline utilization A flavoenzyme from *Bradyrhizobium japonicum*. Proceedings of the National Academy of Sciences of the United States of America 107, 2878-2883

26. White, T. A., Krishnan, N., Becker, D. F., and Tanner, J. J. (2007) Structure and kinetics of monofunctional proline dehydrogenase from *Thermus thermophilus*. J Biol Chem 282, 14316-14327

27. Williams, I., and Frank, L. (1975) Improved chemical synthesis and enzymatic assay of delta-1-pyrroline-5-carboxylic acid. Anal Biochem 64, 85-97

28. Lipinski, C. A., Lombardo, F., Dominy, B. W., and Feeney, P. J. (2001) Experimental and computational approaches to estimate solubility and permeability in drug discovery and development settings. Adv Drug Deliv Rev 46, 3-26

29. Williams, H. J., Williams, N., Spurlock, G., Norton, N., Zammit, S., Kirov, G., Owen, M. J., and Q'Donovan, M. C. (2003) Detailed analysis of PRODH and PsPRODH reveals no association with schizophrenia. Am J Med Genet B Neuropsychiatr Genet 1208, 42-46

30. Willis, A., Bender, H. U., Steel, G., and Valle, D. (2008) PRODH variants and risk for schizophrenia. Amino Acids 35, 673-679

31. Tallarita, E., Pollegioni, L., Servi, S., and Molla, G. (2012) Expression in *Escherichia coli* of the catalytic domain of human proline oxidase. Protein Expres Purif 82, 345-351

32. Pemberton, T. A., and Tanner, J. J. (2013) Structural basis of substrate selectivity of Delta(1)-pyrroline-5-carboxylate dehydrogenase (ALDH4A1): semialdehyde chain length. Arch Biochem Biophys 538, 34-40

33. Ostrander, E. L., Larson, J. D., Schuermann, J. P., and Tanner, J. J. (2009) A Conserved Active Site Tyrosine Residue of Proline Dehydrogenase Helps Enforce the Preference for Proline over Hydroxyproline as the Substrate. Biochemistry 48, 951-959

The foregoing is illustrative of the present invention, and is not to be construed as limiting thereof. The invention is defined by the following claims, with equivalents of the claims to be included therein.

That which is claimed is:

1. A method of inhibiting the formation of oxalate kidney stones, comprising: administering to a subject in need thereof a therapeutically effective amount of a compound of Formula I:

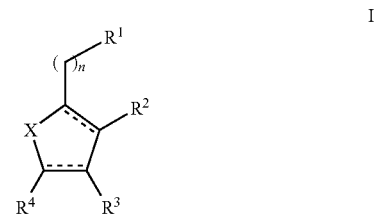

wherein:
 X is O, or $CR^xR^y$, wherein $R^x$ and $R^y$ are each;
 n is 0, 1, 2, 3, 4, 5 or 6;
 $R^1$ is carboxy;
 $R^2$ is selected from the group consisting of: H, alkyl, hydroxy, amine, and =O; or $R^2$ is $R^{2a}R^{2b}$, wherein $R^{2a}$ and $R^{2b}$ are each independently selected from alkyl and hydroxy;
 $R^3$ is selected from the group consisting of: H, hydroxy, amine, and =O; or $R^3$ is $R^{3a}R^{3b}$, wherein $R^{3a}$ and $R^{3b}$ are each hydroxy; and
 $R^4$ is selected from the group consisting of: H, alkyl, and hydroxy; or $R^4$ is $R^{4a}R^{4b}$ wherein $R^{4a}$ and $R^{4b}$ are each independently selected from alkyl, hydroxy, and halo, wherein said alkyl may be unsubstituted or substituted 1, 2 or 3 times with hydroxy;
 or a pharmaceutically acceptable salt thereof.

2. The method of claim 1,
 wherein:
 X is S;
 n is 0;

$R^2$ is selected from the group consisting of: H and lower alkyl;

$R^3$ is selected from the group consisting of: hydroxy, and =O; or $R^3$ is $R^{3a}R^{3b}$, wherein $R^{3a}$ and $R^{3b}$ are each hydroxy; and $R^4$ is selected from the group consisting of: H and lower alkyl;

or a pharmaceutically acceptable salt thereof.

3. A method of inhibiting the production of glyoxylate and/or oxalate in a subject in need thereof, comprising: administering to said subject a therapeutically effective amount of a compound of Formula I:

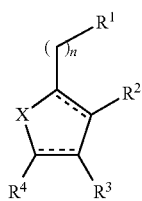

I wherein:
X is O, S or $CR^xR^y$, wherein $R^x$ and $R^y$ are each H;
n is 0, 1, 2, 3, 4, 5 or 6;
$R^1$ is carboxy;
$R^2$ is selected from the group consisting of: H, alkyl, hydroxy, amine, and =O; or $R^2$ is $R^{2a}R^{2b}$, wherein $R^{2a}$ and $R^{2b}$ are each independently selected from alkyl and hydroxy;
$R^3$ is selected from the group consisting of: H, hydroxy, amine, and =O; or $R^3$ is $R^{3a}R^{3b}$, wherein $R^{3a}$ and $R^{3b}$ are each hydroxy; and
$R^4$ is selected from the group consisting of: H, alkyl, and hydroxy; or $R^4$ is $R^{4a}R^{4b}$ wherein $R^{4a}$ and $R^{4b}$ are each independently selected from alkyl, hydroxy, and halo, wherein said alkyl may be unsubstituted or substituted 1, 2 or 3 times with hydroxy;
or a pharmaceutically acceptable salt thereof.

4. The method of claim 3,
wherein:
X is S;
n is 0;
$R^2$ is selected from the group consisting of: H and lower alkyl;
$R^3$ is selected from the group consisting of: H, hydroxy, and =O; or $R^3$ is $R^{3a}R^{3b}$, wherein $R^{3a}$ and $R^{3b}$ are each hydroxy; and
$R^4$ is selected from the group consisting of: H and lower alkyl;
or a pharmaceutically acceptable salt thereof.

5. A method of inhibiting hydroxyproline dehydrogenase (HYPDH) in a subject in need thereof, comprising: administering to said subject a therapeutically effective amount of a compound of Formula I:

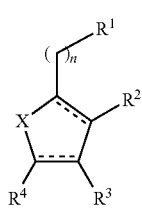

I wherein:
X is O, S or $CR^xR^y$, wherein $R^x$ and $R^y$ are each H;
n is 0, 1, 2, 3, 4, 5 or 6;
$R^1$ is carboxy;
$R^2$ is selected from the group consisting of: H, alkyl, hydroxy, amine, and =O; or $R^2$ is $R^{2a}R^{2b}$, wherein $R^{2a}$ and $R^{2b}$ are each independently selected from alkyl and hydroxy;
$R^3$ is selected from the group consisting of: H, hydroxy, amine, and =O; or $R^3$ is $R^{3a}R^{3b}$, wherein $R^{3a}$ and $R^{3b}$ are each hydroxy; and
$R^4$ is selected from the group consisting of: H, alkyl, and hydroxy; or $R^4$ is $R^{4a}R^{4b}$ wherein $R^{4a}$ and $R^{4b}$ are each independently selected from alkyl, hydroxy, and halo, wherein said alkyl may be unsubstituted or substituted 1, 2 or 3 times with hydroxy;
or a pharmaceutically acceptable salt thereof.

6. The method of claim 5,
wherein:
X is S;
n is 0;
$R^1$ is carboxy;
$R^2$ is selected from the group consisting of: H and lower alkyl;
$R^3$ is selected from the group consisting of: H, hydroxy, and =O; or $R^3$ is $R^{3a}R^{3b}$, wherein $R^{3a}$ and $R^{3b}$ are each hydroxy; and
$R^4$ is selected from the group consisting of: H and lower alkyl;
or a pharmaceutically acceptable salt thereof.

7. The method of claim 1, wherein said compound is selected from the group consisting of:

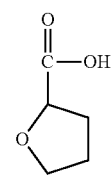

2

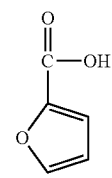

3

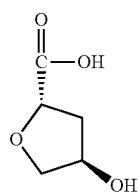

4 and pharmaceutically acceptable salts thereof.

8. The method of claim 1, wherein said compound is selected from the group consisting of:

9. The method of claim 1, wherein said compound is selected from the group consisting of:

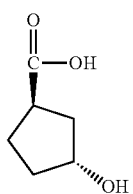 5

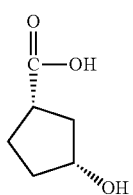 6

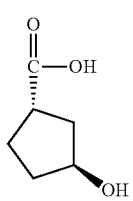 7

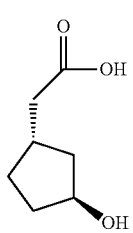 8

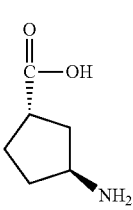 9

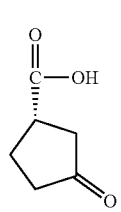 10

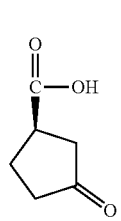 11

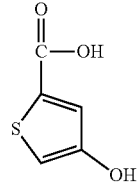 12

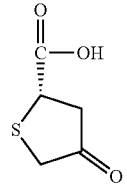 13

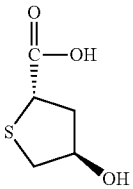 14

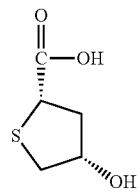 15

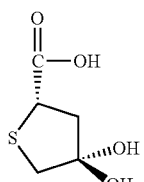 16 and pharmaceutically acceptable salts thereof.

10. The method of claim 1, wherein said subject is a human subject.

11. The method of claim 1, wherein said subject is a non-human animal subject.

12. The method of claim 1, wherein said administering is carried out by administering a pharmaceutical composition comprising said compound or pharmaceutically acceptable salt thereof.

13. The method of claim 3, wherein said subject is a human subject.

14. The method of claim 3, wherein said subject is a non-human animal subject.

15. The method of claim 3, wherein said administering is carried out by administering a pharmaceutical composition comprising said compound or pharmaceutically acceptable salt thereof.

16. The method of claim 5, wherein said subject is a human subject.

17. The method of claim 5, wherein said subject is a non-human animal subject.

18. The method of claim 5, wherein said administering is carried out by administering a pharmaceutical composition comprising said compound or pharmaceutically acceptable salt thereof.

* * * * *

UNITED STATES PATENT AND TRADEMARK OFFICE
CERTIFICATE OF CORRECTION

PATENT NO. : 10,562,844 B2
APPLICATION NO. : 15/545818
DATED : February 18, 2020
INVENTOR(S) : Lowther et al.

Page 1 of 1

It is certified that error appears in the above-identified patent and that said Letters Patent is hereby corrected as shown below:

In the Claims

Column 20, Line 48, Claim 1: Please correct "O, or $CR^xR^y$, wherein $R^x$ and $R^y$ are each;"
to read -- O, S or $CR^xR^y$, wherein $R^x$ and $R^y$ are each H; --

Column 20, Line 67, Claim 2: Please correct "n is O" to read -- n is 0 --

Column 21, Line 43, Claim 4: Please correct "n is O" to read -- n is 0 --

Column 21, Line 47, Claim 4: Please correct "$R^{3A}R^{3b}$" to read -- $R^{3a}R^{3b}$ --

Signed and Sealed this
Twenty-first Day of July, 2020

Andrei Iancu
*Director of the United States Patent and Trademark Office*